(12) United States Patent
Boone et al.

(10) Patent No.: US 10,167,252 B2
(45) Date of Patent: *Jan. 1, 2019

(54) COMPOUNDS AND MIXTURES WITH ANTIDEGRADANT AND ANTIFATIGUE EFFICACY AND COMPOSITIONS INCLUDING SUCH COMPOUNDS

(71) Applicant: Eastman Chemical Company, Kingsport, TN (US)

(72) Inventors: Matthew Allen Boone, Gray, TN (US); Donald L. Fields, Jr., Copley, OH (US); Frederick Ignatz-Hoover, Elyria, OH (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/618,301

(22) Filed: Jun. 9, 2017

(65) Prior Publication Data

US 2017/0275239 A1 Sep. 28, 2017

Related U.S. Application Data

(63) Continuation-in-part of application No. 15/371,257, filed on Dec. 7, 2016.

(60) Provisional application No. 62/270,909, filed on Dec. 22, 2015.

(51) Int. Cl.

| | |
|---|---|
| *C07C 251/20* | (2006.01) |
| *C09K 15/18* | (2006.01) |
| *C07C 249/02* | (2006.01) |
| *C07C 209/52* | (2006.01) |
| *B60C 1/00* | (2006.01) |
| *C07C 211/54* | (2006.01) |
| *C08K 5/18* | (2006.01) |
| *C10L 1/222* | (2006.01) |
| *C10L 1/223* | (2006.01) |
| *C10M 133/12* | (2006.01) |

(52) U.S. Cl.

CPC .............. *C07C 251/20* (2013.01); *B60C 1/00* (2013.01); *C07C 209/52* (2013.01); *C07C 211/54* (2013.01); *C07C 249/02* (2013.01); *C08K 5/18* (2013.01); *C09K 15/18* (2013.01); *C10L 1/223* (2013.01); *C10L 1/2222* (2013.01); *C10M 133/12* (2013.01); *C07C 2601/04* (2017.05); *C10L 2230/08* (2013.01); *C10M 2215/067* (2013.01); *C10N 2230/00* (2013.01)

(58) Field of Classification Search

CPC . C07C 251/20; C07C 211/54; C07C 2601/04; C07C 249/02; C07C 209/52; C10L 1/223; C10L 1/2222; C10L 2230/08; C08K 5/18; B60C 1/00; C09K 15/18; C10N 2230/00; C10M 2215/067; C10M 133/12

See application file for complete search history.

(56) References Cited

U.S. PATENT DOCUMENTS

| | | |
|---|---|---|
| 1,884,889 A | 10/1932 | Semon |
| 2,200,756 A | 5/1940 | Messer et al. |
| 2,905,654 A | 9/1959 | Ambelang |
| 3,398,193 A | 8/1968 | Wheeler |

(Continued)

FOREIGN PATENT DOCUMENTS

| | | | |
|---|---|---|---|
| EP | 2952505 A1 | 12/2015 | |
| GB | 835826 A | * 5/1960 | ............... C08K 5/19 |

(Continued)

OTHER PUBLICATIONS

Oberster et al., Synthesis of Substituted P-phenylenediamines, Feb. 1, 1967, Canadian Journal of Chemistry, vol. 45, p. 165-201 (Year: 1967).*

(Continued)

*Primary Examiner* — Taiwo Oladapo
(74) *Attorney, Agent, or Firm* — Michael Carrier

(57) ABSTRACT

Antidegradant compounds are disclosed, and methods of making them, that are represented by the formula I:

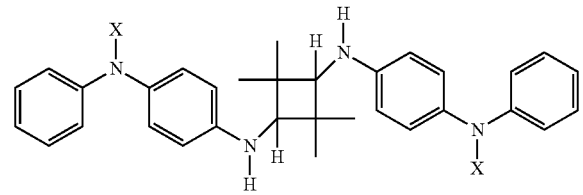

wherein each X is independently selected from the group consisting of ethyl, methyl, or hydrogen.

Also disclosed are diimine intermediates corresponding to formula III:

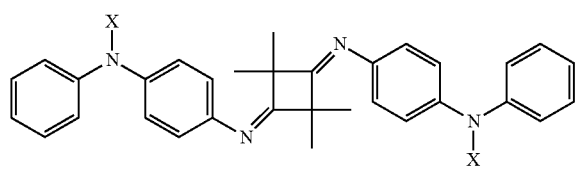

(Continued)

wherein each X is independently selected from the group consisting of ethyl, methyl, or hydrogen. These intermediates themselves exhibit antidegradant activity.

11 Claims, No Drawings

(56) References Cited

U.S. PATENT DOCUMENTS

| | | | |
|---|---|---|---|
| 4,627,929 A * | 12/1986 | Buysch | C10M 169/044 508/254 |
| 5,032,602 A | 7/1991 | Fey | |
| 5,504,159 A | 4/1996 | Sturm et al. | |
| 6,706,217 B2 | 3/2004 | Malz et al. | |
| 7,563,929 B2 | 7/2009 | Hobbs et al. | |
| 8,080,601 B2 | 12/2011 | Patil et al. | |
| 8,080,689 B2 | 12/2011 | Kumar et al. | |
| 8,833,417 B2 | 9/2014 | Da Silva et al. | |
| 8,987,515 B2 | 3/2015 | Rowland | |
| 2005/0159519 A1 | 7/2005 | Nakagome et al. | |
| 2014/0316163 A1 | 10/2014 | Kumar et al. | |
| 2015/0031810 A1 | 1/2015 | Araujo Da Silva et al. | |
| 2017/0166727 A1 | 6/2017 | Saiki et al. | |
| 2017/0320811 A1 | 11/2017 | Yan | |

FOREIGN PATENT DOCUMENTS

| | | |
|---|---|---|
| GB | 835826 A | 5/1960 |
| KR | 20090100099 A | 9/2009 |
| KR | 1364781 | 2/2014 |
| SU | 250151 A1 | 12/1969 |
| WO | WO 2015/077635 A2 | 5/2015 |
| WO | WO 2015-178037 A1 | 11/2015 |
| WO | WO 2015-178038 A1 | 11/2015 |
| WO | WO 2015-178039 A1 | 11/2015 |
| WO | WO 2017-112440 A1 | 6/2017 |

OTHER PUBLICATIONS

Office Action dated Apr. 19, 2018 received in co-pending U.S. Appl. No. 15/618,291.
Bitsi et al., N-Alkylation d'amines en Catalyse Homogene. Sythese de monoet de daimines Cycliques, Sep. 19, 1989, Journal of Oranometallic Chemistry, vol. 373, Issue 3 (Year: 1989).
Office Action dated Apr. 13, 2018 receiving in co-pending U.S. Appl. No. 15/618,288.
Copending U.S. Appl. No. 15/371,257, filed Dec. 7, 2016, Boone et al.
Oberster, A.E, et.al Canadian Journal of Chemistry 1966, 45, 195-201.
Guillena, et.al. Chem. Rev. 2010, 110, 1611.
Centre for Chemical Substances and Preparations, Slovaki; "Justification Document for the Selection of a Corap Substance" http://echa.europa.eu/documents/10162/9801478/corap_justification_448-020-2_sk_en.pdf (Accessed May 11, 2015).
HallStar. "The Use of Antiozonants in Rubber Compounding" http://www.hallstar.com/techdocs/ANTIOZO.pdf (Accessed May 11, 2015).
PCT International Search Report and Written Opinion dated Mar. 9, 2017 for International Application No. PCT/US2016/066085.
Copending U.S. Appl. No. 15/618,281, filed Jun. 9, 2017, Boone et al.
Copending U.S. Appl. No. 15/618,288, filed Jun. 9, 2017, Boone et al.
Copending U.S. Appl. No. 15/618,291, filed Jun. 9, 2017, Boone et al.
Copending U.S. Appl. No. 15/618,298, filed Jun. 9, 2017, Boone et al.
PCT International Search Report and Written Opinion dated Sep. 13, 2018 for International Application No. PCT/US2018/033095.
Guangxun et al., "Investigation and application of amphoteric alpha-amino aldehyde: an in situ generated species based on Heyns rearrangement", Organic Letters, vol. 18, No. 18, Aug. 30, 2016, pp. 4526-4529.
Office Action dated Oct. 5, 2018 received in co-pending U.S. Appl. No. 15/618,288.
Office Action dated Apr. 25, 2018 received in co-pending U.S. Appl. No. 15/371,257.
Office Action dated Apr. 25, 2018 received in co-pending U.S. Appl. No. 15/618,281.
Office Action dated Apr. 26, 2018 received in co-pending U.S. Appl. No. 15/618,298.
Office Action dated Sep. 19, 2018 received in co-pending U.S. Appl. No. 16/103,080.
PCT International Search Report and Written Opinion dated Aug. 28, 2018 for International Application No. PCT/US2018/033107.
Copending U.S. Appl. No. 16/103,080, filed Aug. 14, 2018, Boone et al.
PCT International Search Report and Written Opinion dated Aug. 13, 2018 for International Application No. PCT/US2018/033101.
PCT International Search Report and Written Opinion dated Aug. 21, 2018 for International Application No. PCT/US2018/033106.
PCT International Search Report and Written Opinion dated Sep. 11, 2018 for International Application No. PCT/US2018/033104.

* cited by examiner ic fluids,
COMPOUNDS AND MIXTURES WITH ANTIDEGRADANT AND ANTIFATIGUE EFFICACY AND COMPOSITIONS INCLUDING SUCH COMPOUNDS

RELATED APPLICATIONS

This continuation-in part application claims the priority benefit of U.S. Nonprovisional patent application Ser. No. 15/371,257 filed Dec. 7, 2016, which in turn claims priority to Provisional Patent Application Ser. No. 62/270,909, titled "COMPOUNDS WITH ANTIDEGRADANT AND ANTIFATIGUE EFFICACY AND COMPOSITIONS INCLUDING SAID COMPOUNDS," filed Dec. 22, 2015, the entire disclosures of which are incorporated herein by reference.

FIELD OF THE INVENTION

The present invention relates generally to compounds, and methods of making them, that have antidegradant and antifatigue efficacy and are useful as an additive for vulcanized rubber articles, vulcanizable elastomeric formulations, lubricants, fuels, fuel additives and other compositions which require such efficacy or in compositions which are themselves useful as compositions to impart such efficacy.

BACKGROUND OF THE INVENTION

Many materials such as plastics, elastomers, lubricants, cosmetics and petroleum products (such as hydraulic fluids, oils, fuels and oil/fuel additives for automotive and aviation applications) are prone to degradation upon prolonged exposure to light, heat, oxygen, ozone, repetitive mechanical actions and the like. Accordingly, compounds and compositions demonstrating antidegradant efficacy are well known the art. For example, U.S. Pat. No. 8,987,515 discloses an aromatic polyamine useful in inhibiting oxidative degradation particularly in lubricant compositions. U.S. Patent Application Publication number 2014/031613 discloses antioxidant macromolecules with purported improved solubility in many commercially available oils and lubricants.

Antidegradants useful in the manufacture of articles formed from elastomers, plastics and the like require a very specific combination of qualities that can be difficult to achieve. While the antidegradants must obviously have commercially acceptable efficacy, they must also exhibit that efficacy over prolonged periods of time associated with use of the article, particularly at exposed surfaces of the article where degradation from environmental factors such as light, oxygen and ozone primarily occurs. Just as important to the protection of surface exposed components, efficacy in protecting imbedded components of composite materials from the effects of oxidative aging and repetitive mechanical action are critically important. The antidegradants must achieve these results while not negatively impacting other additives' efficacy or desirable characteristics in the final article. Further, antidegradants which provide or improve the mechanical fatigue life after an article has been in service, aged oxidatively or by exposure to ozone are highly valued since these will inherently improve the useful mechanical service life of article. Consequently, elastomeric articles which undergo repeated mechanical flexure, extension, or compression during service would greatly benefit from such a discovery.

Articles formed from general purpose elastomers such as natural rubber, in particular tires, are especially prone to degradation from both oxygen and ozone. As discussed in U.S. Pat. No. 2,905,654, the effect on rubber from degradation by oxygen is different from the effect from degradation from ozone; however, both effects can be detrimental to tire performance, appearance and life expectancy. Fatigue and crack propagation are also issues of specific concern, in particular for steel belt edge areas and tire sidewalls which are subject to significant stresses and stretching forces while flexed whether inflated, partially inflated and throughout the service life of the tire. U.S. Pat. No. 8,833,417 describes an antioxidant system that purportedly increases long-term resistance to fatigue and crack propagation over the known antioxidants discussed immediately below.

Materials with antidegradant efficacy are well known in the art for use in tire applications and are commercially available. For example, N,N'-disubstituted-paraphenylenediamines such as those sold by Eastman Chemical Company under the trademark Santoflex® are generally favored by many tire manufacturers for this purpose. EP Pat. Appln. Publn. No. EP 3 147 321 A1 discloses rubber compositions, tires, amine compounds, and anti-aging agents, and in particular, a rubber composition that is said to be suitable for use in tread rubber or sidewall rubber of a tire. As governmental regulation, market needs and customer expectations push the rubber industry toward lighter weight tires to enhance fuel efficiency and conserve natural resource feedstocks, a continuing need nonetheless exists for improved antidegradants that exhibit (i) multiple efficacies against fatigue, crack propagation and the various mechanisms of degradation; (ii) increased efficacy, especially at lower concentrations and (iii) longer efficacy periods when compared to current commercial materials.

SUMMARY OF THE INVENTION

In one aspect, the present invention relates to compounds represented by the formula I:

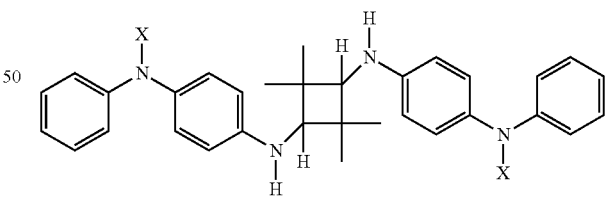

wherein each X is independently selected from the group consisting of ethyl, methyl, or hydrogen.

In another aspect, the present invention relates to compositions and mixtures including a compound represented by formula I above.

In a further aspect, the present invention relates to methods of making antidegradant compounds, and mixtures containing them, that correspond to formula I as set out above and as further described herein. In this aspect, a p-phenylenediamine corresponding to formula IV:

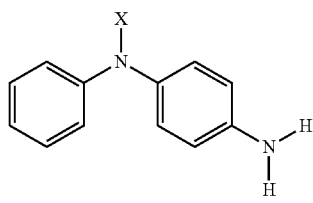

wherein each X is independently selected from the group consisting of ethyl, methyl, or hydrogen;

is reacted with a dicarbonyl or dione corresponding to formula II:

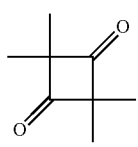

II to thereby obtain a diimine corresponding to formula III:

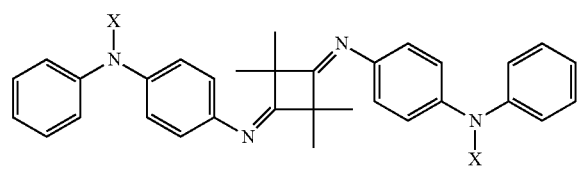

III

The diimine corresponding to formula III may then be reduced or hydrogenated to obtain a mixture that includes the antidegradant compound according to formula I:

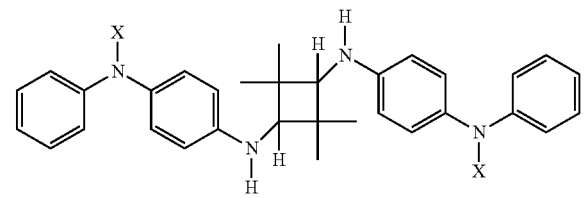

I wherein each X is independently selected from the group consisting of ethyl, methyl, or hydrogen.

In yet another aspect, the present invention relates to other methods of making the antidegradant compounds, and mixtures containing them, that correspond to formula I as set out above and as further described herein. In this aspect, a p-phenylenediamine corresponding to formula IV:

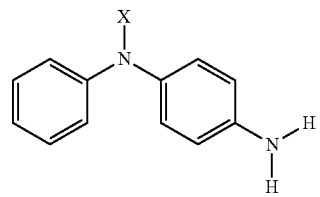

IV wherein each X is independently selected from the group consisting of ethyl, methyl, or hydrogen;
is reacted with a diol corresponding to formula V:

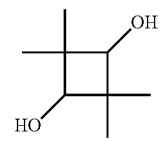

V to thereby obtain a diimine corresponding to formula III:

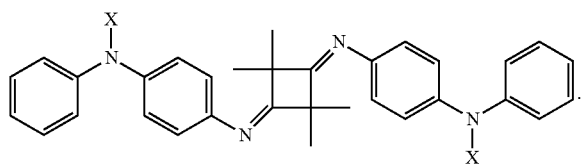

III

The diimine corresponding to formula III may then be reduced or hydrogenated to obtain a mixture that includes the antidegradant compound according to formula I:

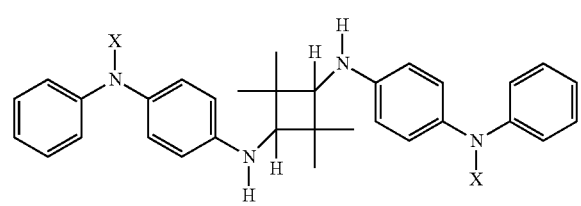

I wherein each X is independently selected from the group consisting of ethyl, methyl, or hydrogen.

In a further aspect, a mixture of a diol and a dione may be used as reactants, in which a p-phenylenediamine corresponding to formula IV:

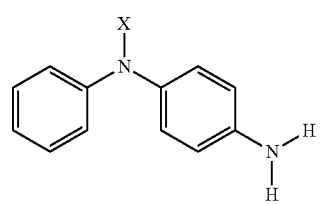

IV wherein each X is independently selected from the group consisting of ethyl, methyl, or hydrogen;
is reacted with one or more of:
a dicarbonyl corresponding to formula II:

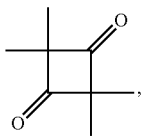

or a diol corresponding to formula V:

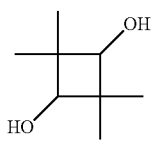

to thereby obtain a diimine corresponding to formula III:

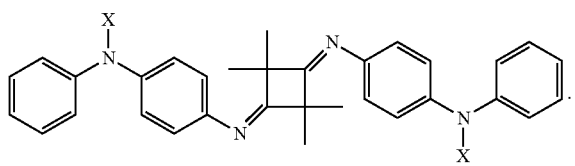

The diimine corresponding to formula III may then be reduced or hydrogenated to obtain a mixture that includes the antidegradant compound according to formula I:

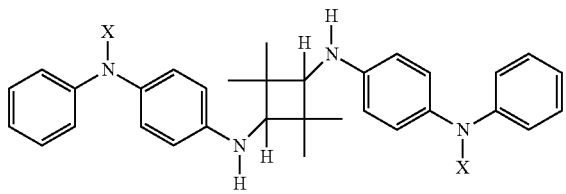

wherein each X is independently selected from the group consisting of ethyl, methyl, or hydrogen.

In yet another aspect, the invention relates to diimines corresponding to formula III:

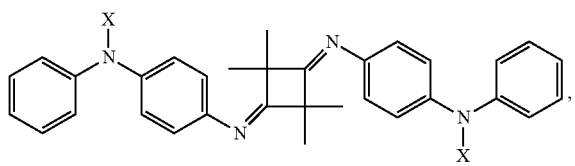

wherein each X is independently selected from the group consisting of ethyl, methyl, or hydrogen. As disclosed herein, these diimines are useful as intermediates to form the antidegradant compounds disclosed and claimed herein that correspond to formula I. We have also found that these diimines themselves have antidegradant properties, although our initial work suggests that the reduced compounds of formula I may have greater activity.

In a further aspect, the present invention is directed to an antidegradant composition including the compounds of the present invention.

In another aspect, the present invention is directed to a lubricant composition including the compounds of the present invention.

In yet another aspect, the present invention is directed to a vulcanizable elastomeric formulation including the compounds of the present invention.

In still another aspect, the present invention is directed to a vulcanized elastomeric rubber article with at least one component formed from a vulcanizable elastomeric formulation of the present invention.

The compounds of the present invention demonstrate antidegradant efficacies and are therefore useful in imparting resistance to crack propagation, degradation and the many manifestations thereof in a variety of applications. When utilized as a component in vulcanizable elastomeric formulations for forming vulcanized rubber articles, and specifically in vehicle tires and their components, we expect the compounds of the present invention will demonstrate a particularly desirable efficacy against oxidative degradation, ozonative degradation and resistance against fatigue and crack propagation that is comparable with or superior to the combination heretofore achieved by prior art materials. Further advantages and areas of applicability will become apparent from the description provided herein. It should be understood that the description and specific examples are intended for purposes of illustration only and are not intended to limit the spirit and scope of the present invention.

DETAILED DESCRIPTION

As utilized herein, the following terms or phrases are defined as follows:

"Antidegradant" refers to a material that inhibits degradation (as caused by for example, through heat, light, oxidation, and/or ozonation), or manifestations thereof, of a composition, formulation or article to which it is added or applied.

"Antifatigue agent" refers to a material that improves the flex fatigue resistance of a composition, formulation or article to which it is added or applied after a period of in-service application time whereby the composition, formulation or article is subjected to thermal, oxidative, ozone and mechanical degradative forces.

"Antioxidant" refers to a material that inhibits oxidative degradation of a composition, formulation or article to which it is added or applied.

"Antiozonant" refers to a material that inhibits ozone exposure degradation of a composition, formulation or article to which it is added or applied.

"Elastomer" means any polymer which after vulcanization (or crosslinking) and at room temperature can be stretched under low stress to at least twice its original length and, upon immediate release of the stress, will return with force to approximately its original length, including without limitation rubber.

"Vulcanizable Elastomeric Formulation" means a composition that includes an elastomer and that is capable of vulcanization when placed under vulcanization conditions.

In a first aspect, the present invention is directed to a compound represented by the formula I:

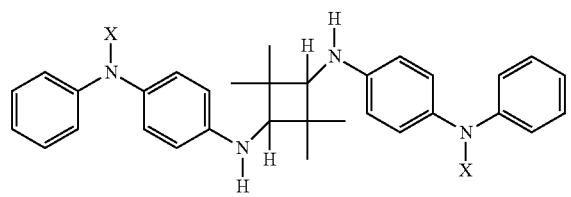

I wherein each X is independently selected from the group consisting of ethyl, methyl, or hydrogen.

Non-limiting examples of the compound of the present invention according to formula I include 2,2,4,4-tetramethylcyclobutane-1,3-diyl) bis (N-phenylbenzene-1,4 diamine, which is represented schematically as:

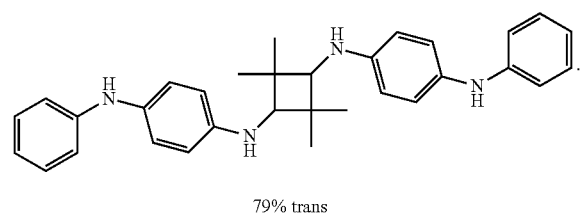

79% trans

Although in one example, the product mixture obtained contained approximately 79% trans conformation, the invention is not intended to be so limited, and comprises mixtures that are predominantly trans conformation, predominantly cis conformation, or any mixtures of the two, cis and trans, conformations, as well as embodiments comprising substantially all trans, or all cis, conformations.

In a related aspect, the present invention relates to compositions including the compounds represented by formula I above, as further elaborated below.

In a further aspect, the present invention relates to methods of making antidegradant compounds, and mixtures containing them, that correspond to formula I as set out above and as further described herein. In one aspect, in which a dicarbonyl may be used as a reactant, a p-phenylenediamine corresponding to formula IV:

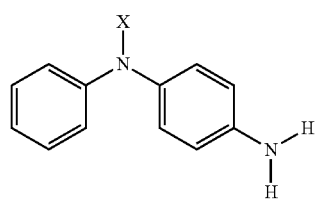

IV wherein each X is independently selected from the group consisting of ethyl, methyl, or hydrogen;

is reacted with a dicarbonyl corresponding to formula II:

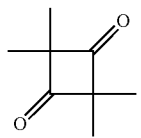

II to thereby obtain a diimine corresponding to formula III:

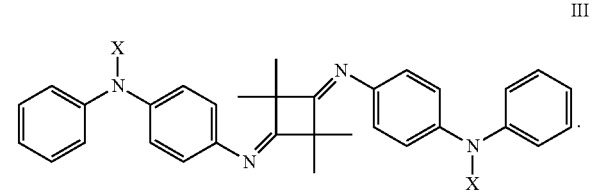

III

The diimine corresponding to formula III may then be reduced or hydrogenated to obtain a mixture that includes the antidegradant compound according to formula I:

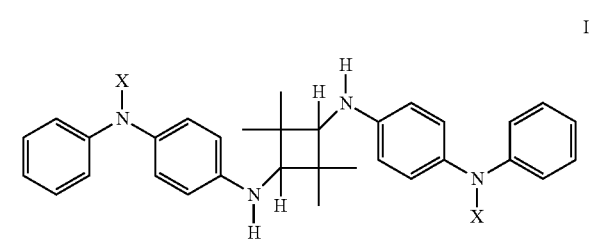

I wherein each X is independently selected from the group consisting of ethyl, methyl, or hydrogen.

Alternatively, the invention relates to processes in which a diol is used, in which a p-phenylenediamine corresponding to formula IV:

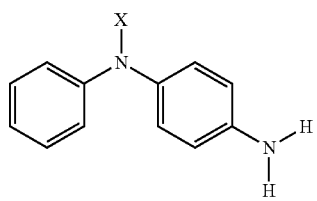

IV wherein each X is independently selected from the group consisting of ethyl, methyl, or hydrogen;

is reacted with a diol corresponding to formula V:

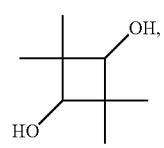

V to thereby obtain a diimine corresponding to formula III:

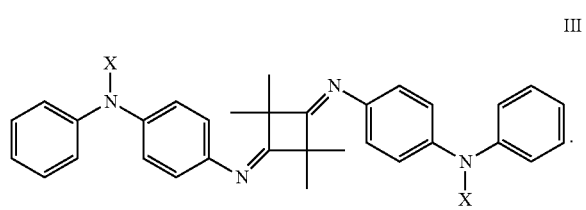

The diimine may then be reduced or hydrogenated to obtain a mixture that includes the antidegradant compound according to formula I, as described herein.

In yet another aspect, a mixture of a diol and a dione may be used, in which a p-phenylenediamine corresponding to formula IV:

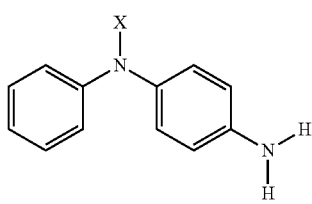

wherein each X is independently selected from the group consisting of ethyl, methyl, or hydrogen;
is reacted with one or more of:
a dicarbonyl corresponding to formula II:

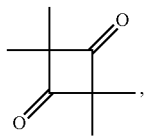

or a diol corresponding to formula V:

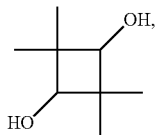

to thereby obtain a diimine corresponding to formula III:

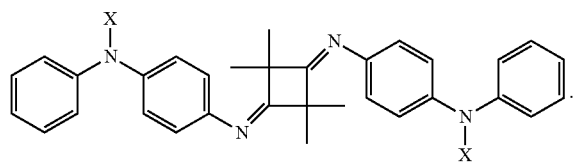

The diimine corresponding to formula III may then be reduced or hydrogenated to obtain a mixture that includes the antidegradant compound according to formula I:

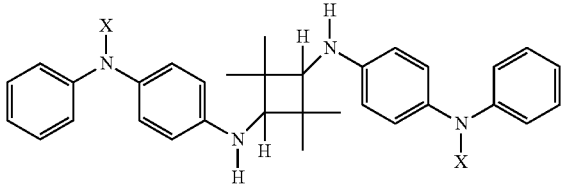

wherein each X is independently selected from the group consisting of ethyl, methyl, or hydrogen.

In a further aspect, the invention relates to diimines corresponding to formula III:

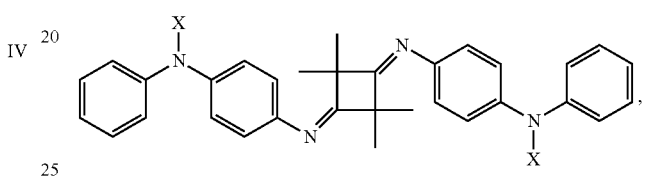

wherein each X is independently selected from the group consisting of ethyl, methyl, or hydrogen. As disclosed herein, these diimines are useful as intermediates to form the antidegradant compounds disclosed and claimed herein that correspond to formula I. Further, we have also found that these diimines themselves exhibit antidegradant properties.

According to the invention, the step of reacting the p-phenylenediamine with the dicarbonyl and/or the diol, and the step of reducing the diimine obtained, may be carried out in sequence, with optional isolation of the intermediate diimine compound, or may be carried out simultaneously in the same reaction mixture, as further described herein.

Suitable p-phenylenediamines useful according to the invention that correspond to formula IV include those in which X is selected from methyl, ethyl and hydrogen; and especially those in which X is hydrogen or methyl, and especially 4-aminoparaphenylenediamine According to the present invention, suitable dicarbonyls include especially 2,2,4,4-Tetramethcylobutanedione. Similarly, suitable diols include 2,2,4,4-Tetramethcylobutanediol.

The diimines corresponding to formula III thereby obtained include especially those in which X is hydrogen, ethyl or methyl.

The antidegradant compounds of the invention corresponding to formula I as described herein are obtained by reduction or hydrogenation of the diimines corresponding to formula III, as described hereinafter.

According to the invention, diimines corresponding to formula III may be prepared by contacting a p-phenylenediamine represented by formula IV with a dicarbonyl represented by formula II, or a diol represented by formula V, in the presence of a solvent. Preferred p-phenylenediamines include those in which X corresponds to methyl, ethyl or hydrogen, and especially hydrogen, that is, 4-aminodiphenylamine (4-ADPA, or 4-aminoparaphenylenediamine).

In preparing the diimines of formula III according to the invention, the solvent may be an alcohol, such as, but not limited to, methanol, ethanol, isopropanol, and n-butanol, or may be an organic solvent such as hexane, cyclohexane, heptane, toluene, methyl acetate, ethyl acetate, butyl acetate, and mixtures thereof. The reaction may be carried out, if necessary or desirable, in the presence of an acid catalyst such as formic acid, acetic acid, propionic acid, p-toluenesulfonic acid, camphorsulfonic acid, HCl, $H_2SO_4$, $H_3PO_4$, or mixtures thereof.

The temperature of the reaction to form the diimine may be carried out, for example, at temperatures from about 0° C. to about 150° C., or from 0° C. to 100° C., or from 5° C. to about 75° C., or from 40° C. to 60° C. The product becomes insoluble in the reaction mixture allowing for ease of separation and purification. For example, the reaction mixture may be cooled to ambient temperature for a period of time, the solids filtered and washed, for example with $NaHCO_3$, followed by one or more washings with water. The filter cake may then be washed, for example in a mixture of an alcohol such as isopropanol and an organic solvent such as heptane. The solids may then be dried, for example in a 50° C. vacuum oven with nitrogen sweep, to obtain the diimine. Each of the parameters described may impact the reaction kinetics, conversion, and selectivity. It may be preferred that reaction conditions are selected such that time required for completion is 0.5 hrs to 36 hrs.

According to the invention, the antidegradant compounds of I are prepared by reduction or hydrogenation of the precursor diimines such as those obtained as just described. This reduction may be carried out in the presence of a solvent and with either 1) a homogeneous or heterogeneous metal catalyst in the presence of hydrogen gas or formic acid or formic acid salt, or 2) a reducing agent.

The solvent can be selected from those commonly used in hydrogenation reactions. Examples of such solvents include but are not limited to methanol, ethanol, isopropanol, butanol, cyclohexane, ethylene glycol, tert-butyl methyl ether, tetrahydrofuran, acetic acid, dimethylformamide, dimethylacetamide, N-methylpyrrolidone, N-butylpyrrolidone, methyl acetate, ethyl acetate, butyl acetate, diethylene glycol monobutyl ether, methyl isobutyl ketone. These solvents can be used individually or in combination as a mixture.

When dimethylformamide or dimethlacetamide are used as a solvent or as part of a solvent mixture, it has been observed that the hydrogenation reaction conditions can lead to the release of some concentration of dimethylamine. The presence of the liberated amine may have a beneficial impact on the selectivity of the catalytic hydrogenation reaction. It may be therefore desireable to add exogeneous dimethylamine or other amines to a reaction when DMF is not present. Examples of such amines include, but are not limited to, methylamine, dimethylamine, triethylamine, pyridine, piperidine, piperazine, DABCO, DBU, and mixtures thereof.

The amount of solvent used is based on the amount of diimine represented by formula III such that the weight % catalyst ranges from about 1 to about 75%, or from 5 to 50%, or from 25-40%, excluding water content, based on the amount of diimine present.

Examples of metal catalysts that can be used for hydrogenation or reduction include, but are not limited to, palladium on carbon, palladium on alumina, platinum on carbon, sulfided platinum on carbon, platinum on alumina, platinum on silica, platinum oxide, Raney nickel, Raney cobalt, ruthenium on carbon, ruthenium on alumina, and a homogenous metal catalyst such as chlorotris(triphenylphosphine)rhodium(I) (Wilkinson's catalyst).

The amount of catalyst used may be based on the amount of diimine represented by formula II such that the weight % catalyst ranges from about 0.005 to about 20% by weight of active catalyst excluding water content, with respect to the amount of diimine present.

The hydrogen pressure used in the catalytic hydrogenation can vary widely, and may range from about atmospheric pressure to about 2,000 psig, or from atmospheric to 500 psig, or at approximately atmospheric pressure. Alternatively, formic acid or formic acid salts can serve as the source of hydrogen for the reduction.

The temperature of the reaction can range from ambient temperature up to 250° C.

Each of the above parameters impact the reaction kinetics, conversion, and selectivity. It is preferred that reaction conditions are selected such that time required for completion is from about 30 minutes to about 12 hrs, or from 1-3 hrs.

For reductions of the diimines to obtain the antidegradant compounds of the invention, reducing agents such as di-isobutyl aluminum hydride and lithium aluminum hydride may be used in combination with a solvent such as diethyl ether, tetrahydrofuran, or tert-butylmethyl ether. Sodium borohydride, lithium borohydride, and sodium cyanoborohydride can also be used in combination with solvents such as methanol, ethanol, and isopropanol. 1H-Benzotriazole can also be used as an additive in combination with borohydride reduction conditions.

A mixture of the disclosed diamine products according to formula 1 and an alky, aryl p-phenylenediamine such as 6PPD (N-(4-methylpentan-2-yl)-N-phenylbenzene-1,4-diamine) or PPPD can be produced by using a ketone such as MIBK or acetone, respectively, as the hydrogenation reaction solvent (see the examples). Such a product may be desirable to produce an antidegradant product mixture having two different migration characteristics. The reaction proceeds with hydrogenation of the diimine to form the diamine. Concomitantly, the ketone solvent will react with any residual 4-ADPA in the diimine starting material, any added additional 4-ADPA and/or any 4-ADPA from hydrolysis of the diimine to form the alkylaryl p-phenylenediamine.

In another aspect briefly referenced above, the present invention is directed to a composition that includes at least one compound of the present invention as described above. The specific amount of the compound of the present invention that is included in the composition may vary widely depending on the intended use application for the composition. It will be understood by one of ordinary skill in the art that the composition of the present invention can include one or more compounds of the present invention such that the concentration of each individual compound necessary to achieve the desired antidegradant efficacy is lower. Further, other known antidegradant additives may be included in the composition such that a reduced amount of the compound of the present invention may be required to achieve the total desired antidegradant efficacy.

In one embodiment that is exemplified in detail above, the composition of a present invention is a vulcanizable elastomeric formulation. The vulcanizable elastomeric formulation of the present invention includes at least one elastomer and the compound of the present invention. Preferably, the compound of the present invention is present in the vulcanizable elastomeric formulation in an amount of from 0.1 to 20.0 parts, preferably from 0.1 to 5.0 parts, per 100 parts elastomer.

The elastomer in the vulcanizable elastomeric formulation may be any vulcanizable unsaturated hydrocarbon elastomer known to one skilled in the art. These elastomers may include without limitaton natural rubber or any synthetic rubber, for example diene containing elastomers such as polymers formed from butadiene; isoprene; or combinations of styrene and butadiene, or styrene and isoprene, or styrene, butadiene and isoprene; or polymers formed from ethylene, propylene and diene monomers such as ethylidene norbonadiene or 1,5-hexadiene. The vulcanizable elastomeric formulation may optionally also include other additives conventionally used in rubber processing, such as processing/flow aids, extenders, plasticizers, resins, adhesion promoters, bonding agents, buffers, fillers, pigments, activators, prevulcanization inhibitors, acid retarders, accelerators, fatty acids, zinc oxide, or other compounding ingredients or additives to further enhance the characteristics and/or improve the performance of the vulcanizable elastomeric formulation or the vulcanized elastomeric article from which it is formed Suitable accelerators may include, but not be limited to guanidines, thiazoles, sulfenamides, sulfenimides, dithiocarbamates, xanthates, thiurams, and combinations or mixtures thereof.

The vulcanizable elastomeric formulation of the present invention is useful in the manufacture of vulcanized elastomeric articles such as rubber belts and hoses, windshield wiper blades, vehicle tires and components thereof such as the tread, shoulder, sidewall and innerliner. Accordingly, in another aspect, the present invention is directed to a vulcanized elastomeric article with at least one component formed from the vulcanizable elastomeric formulation of the present invention. In one particular embodiment, the vulcanized elastomeric article is a vehicle tire and the tire component is a sidewall.

The compounds of the present invention may thus be prepared from a polyalcohol starting material through a hydrogen autotransfer procedure using a homogenous or heterogeneous catalyst (see e.g. Guillena, et. al. *Chem. Rev.* 2010, 110, 1611 for a general description of the mechanism). The compounds of interest can also be prepared from a polycarbonyl starting material using a heterogeneous transition metal catalyst in the presence of hydrogen.

Precursors for compounds of the present invention, the compounds of the present invention and methods for their manufacture are illustrated by the following examples, which are not intended in any way to limit the spirit or scope of the present invention.

The compounds of the present invention may also be synthesized by a catalytic reductive alkylation method from a polycarbonyl starting material and involving a heterogeneous transition metal catalyst in the presence of hydrogen. Examples of these methods are provided below.

Example 1: Preparation of Precursor (N,N',N,N')—N,N'-(2,2,4,4-tetramethylcyclobutane-1,3-diylidene)bis(N-phenylbenzene-1,4-diamine)

2,2,4,4-Tetramethcylobutanedione (10 g, 71 mmol) and 4-aminodiphenylamine (4-ADPA) (33 g, 180 mmol) were transferred to a 3-necked 500 mL round-bottom flask equipped with a magnetic stir bar and thermocouple. Toluene (143 mL) was added, followed by a catalytic amount of p-toluenesulfonic acid (2.03 g). A Dean-Stark with condenser was placed on the flask, and the mixture was heated to reflux. After 18.5 hrs, heating was discontinued. The mixture was cooled to ambient temperature. Heptane (ca. 200 mL) was added. The solids were collected by filtration and washed with a saturated solution of NaHCO$_3$ and then water. The dark blue solids were then washed with 100 mL of CH$_2$Cl$_2$. The desired product (shown as 1 in the above schematic) was isolated as a light gray solid CH NMR indicated a mixture of E/Z imine isomers) (30.1 g, 89% yield). Tm=258.9° C. $^1$H NMR (300 MHz, CDCl$_3$) δ 7.25 (m, 6H), 7.15-6.25 (m, 12H), [2.94 (s), 2.72 (s), 2.53 (s) 12H total, 67% trans geometry]. In addition to serving as a precursor for the antidegradant compound of Example 2, we have found, as shown in the OIT testing discussed below, that this diimine itself exhibits antidegradant activity, although our preliminary work suggests that the reduced compound exhibits higher activity.

Example 2: Preparation of N,N'-(2,2,4,4-tetramethylcyclobutane-1,3-diyl)bis(N-phenylbenzene-1,4-diamine)

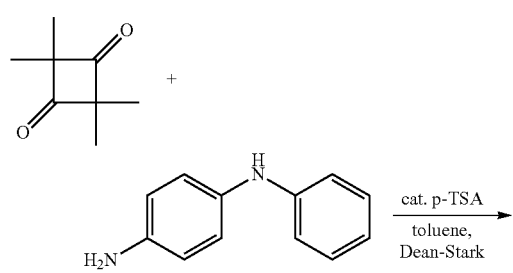

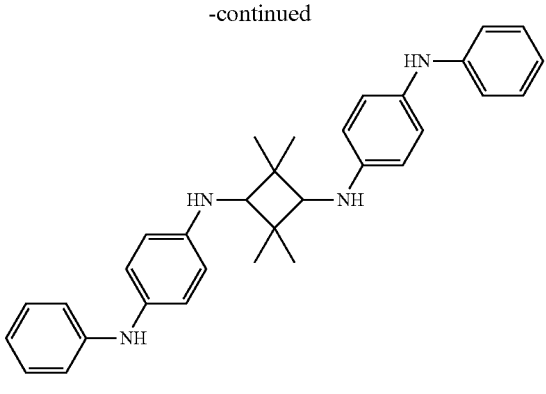

2

LiAlH4 (8.45 g, 223 mmol) was carefully added to THF (223 mL) in a 1 L round-bottom flask. The di-imine (26.3 g, 55.7 mmol) was carefully added to the solution. After the addition was complete, the reaction was refluxed for 4 hrs. After this time, the mixture was cooled using an ice water bath and then carefully quenched by the drop wise addition of water (10 mL) followed by drop wise addition of 15% NaOH (20 mL). The mixture was stirred overnight. After filtration, the brown liquid was concentrated under reduced pressure using a rotary evaporator. The product (shown as 2 in the above schematic) was isolated as a tan solid (24.6 g, 93% yield). ($^1$H NMR indicated a mixture of cis-trans isomers). Tm=179.5° C. $^1$H NMR (300 MHz, CDCl$_3$) δ 8.56 (m, 4H), 8.37 (m, 4H), 8.23-8.13 (m, 6H), 8.02-7.94 (m, 4H). 6.76 (bs, 2H), 5.28-5.13 (m, 2H), [4.77 (bs), 4.71 (bs) 2H total, 81% trans], [2.76 (s), 2.61 (s), 2.43 (s) 12H total]

In order to demonstrate the efficacies of the compounds of the present invention, analytical procedures to measure oxygen degradation inhibition were performed. To demonstrate antioxidant efficacy, the oxidative induction time (OIT) of selected examples were evaluated. OIT is measured according to a procedure carried out in a differential scanning calorimeter (DSC) and is used by those of ordinary skill in the art to predict thermo-oxidative performance of a material. In this procedure, samples held in a sample cell and heated under a nitrogen atmosphere to a preselected temperature (for the present application 150° C.). Oxygen is then introduced to the sample cell and the length of time before the onset of degradation, as seen by the initiation of an endothermic process in the DSC trace, is measured. [N-(1,3-Dimethylbutyl)-N'-phenyl-p-phenylenediamine (6PPD, or N-(4-methylpentan-2-yl)-N-phenylbenzene-1,4-diamine) is a known antidegradant additive for rubber that is commercially available from Eastman Chemical Company under the trademark Santoflex®, was also tested as a control for OIT. The results are listed in the following table:

TABLE 1

Oxidative Induction Time (OIT) measured at 150° C.

| Example | OIT at 150° C. (minutes) |
|---|---|
| no additive | 2 |
| 6-PPD (control) | 43 |
| 1 | 31 |
| 2 | 53 |

As indicated by the above data, the compounds of the present invention demonstrate antioxidant performance that compares well to 6PPD and indicates utility in fuels, lubes, tires and other applications that can benefit from a highly active antioxidant compound).

While the foregoing aspects of the present invention have described utilities primarily focused in the area of compositions related to vulcanized elastomeric article manufacture, it will be understood that the compounds of the present invention may also be useful in compositions for other utilities where antioxidant and/or antiozonant efficacy is desired. According and as described above, the present invention in a general aspect is directed to a composition including the compound of the present invention. In one embodiment, the composition is an antidegradant composition with utility and efficacy for inhibition of degradation of a composition, formulation or article to which it is added or applied. The antidegradant composition of the present invention therefore includes the compound of the present invention and optionally a carrier for the compound. Suitable carriers are substantially inert with respect to the compound and include waxes, oils, or solids such as carbon black or silica.

In a separate embodiment, the composition of the present invention has a separate primary utility or functionality (such as a coating, lubricant, oil, fuel additive or fuel composition) and includes a functional ingredient and the compound of the present invention as a component. The functional ingredient is typically a degradable material such as a hydrocarbon but may also include other degradable materials. This embodiment therefore encompasses for example, a lubricant composition that includes a lubricant as the functional ingredient and the compound of the present invention. This embodiment further encompasses a combustible fuel composition that includes a combustible fuel as the functional ingredient and the compound of the present invention. This embodiment further encompasses a fuel additive composition that includes a fuel additive as the functional ingredient and the compound of the present invention.

A person skilled in the art will recognize that the measurements described herein are standard measurements that can be obtained by a variety of different test methods. The test methods described represents only one available method to obtain each of the required measurements.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:
1. An antidegradant compound represented by formula I:

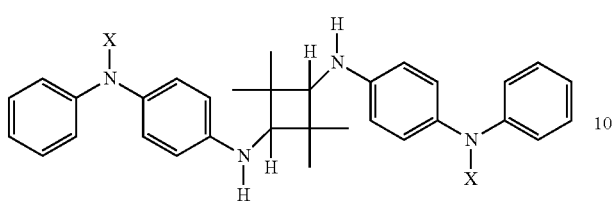

I wherein each X is independently selected from the group consisting of ethyl, methyl, or hydrogen.
2. The compound of claim 1, wherein each X is hydrogen.
3. The compound of claim 1, wherein each X is methyl.
4. A method of making the antidegradant compound of claim 1, comprising:
reacting, a p-phenylenediamine corresponding to formula IV:

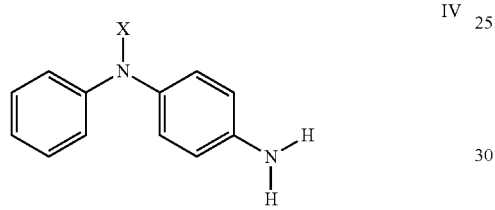

IV wherein each X is independently selected from the group consisting of ethyl, methyl, or hydrogen,
with a dicarbonyl corresponding to formula

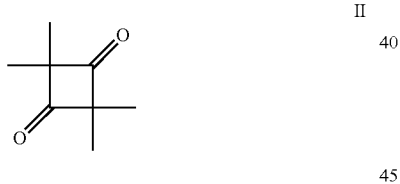

II to thereby obtain a diimine; and
reducing or hydrogenating the diimine to obtain a mixture that includes the antidegradant compound.
5. The method of claim 4, wherein the p-phenylenediamine is reacted with the dicarbonyl in the presence of an acid catalyst.
6. A method of making the antidegradant compound of claim 1, comprising:
reacting a p-phenylenediamine corresponding to formula IV:

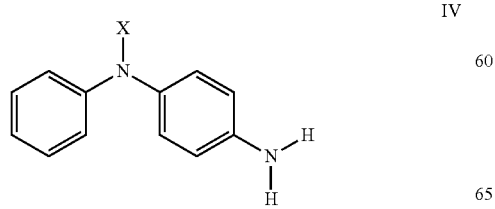

IV wherein each X is independently selected from the group consisting of ethyl, methyl, or hydrogen,
with a diol corresponding to formula V:

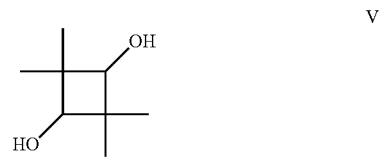

V to thereby obtain a diimine; and
reducing or hydrogenating the diimine to obtain a mixture that includes the antidegradant compound according to formula I.
7. The method of claim 6, wherein the p-phenylenediamine is reacted with the dicarbonyl in the presence of an acid catalyst.
8. A method of making the antidegradant compound of claim 1, comprising:
reacting a p-phenylenediamine corresponding to formula IV:

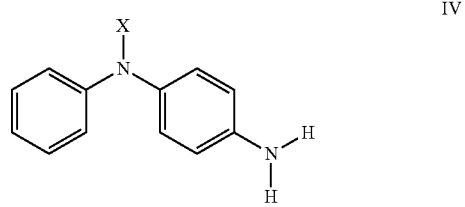

IV wherein each X is independently selected from the group consisting of ethyl, methyl, or hydrogen,
with one or more of:
a dial corresponding to formula V;

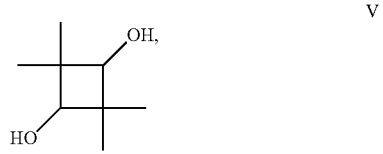

V or
a dicarbonyl corresponding to formula II:

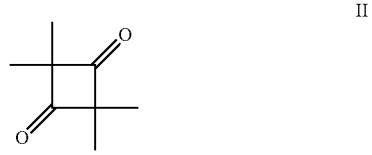

II to thereby obtain a diimine; and
reducing or hydrogenating the diimine to obtain a mixture that includes the antidegradant compound according to formula I.
9. The method of claim 8, wherein the p-phenylenediamine is reacted with the diol or the dicarbonyl in the presence of an acid catalyst.

10. A diimine corresponding to formula III:

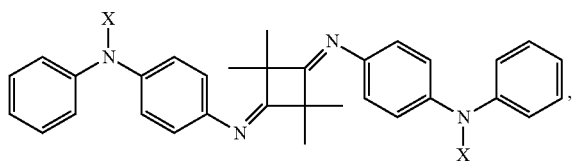

wherein each X is independently selected from the group consisting of ethyl, methyl, or hydrogen.

11. A method of making the diimine of claim 10, comprising:

reacting a p-phenylenediamine corresponding to formula IV:

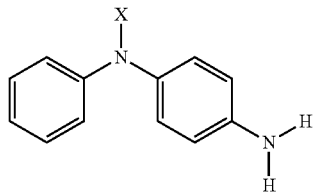

wherein each X is independently selected from the group consisting of ethyl, methyl, or hydrogen, with one or more of:

a diol corresponding to formula V:

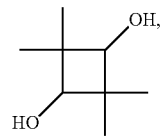

or a dicarbonyl corresponding to formula II:

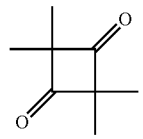

to thereby obtain the diimine.

* * * * *